(12) United States Patent
Girouard et al.

(10) Patent No.: US 11,026,645 B2
(45) Date of Patent: Jun. 8, 2021

(54) RADIOGRAPHY BACKSCATTER SHIELDS AND X-RAY IMAGING SYSTEMS INCLUDING BACKSCATTER SHIELDS

(71) Applicant: Illinois Tool Works Inc., Glenview, IL (US)

(72) Inventors: Brian Girouard, Billerica, MA (US); Jason Bourn, Stratham, NH (US); Paul Benson, Waltham, MA (US)

(73) Assignee: Illinois Tool Works Inc., Glenview, IL (US)

(*) Notice: Subject to any disclaimer, the term of this patent is extended or adjusted under 35 U.S.C. 154(b) by 28 days.

(21) Appl. No.: 16/269,457

(22) Filed: Feb. 6, 2019

(65) Prior Publication Data
US 2019/0239830 A1 Aug. 8, 2019

Related U.S. Application Data

(60) Provisional application No. 62/627,466, filed on Feb. 7, 2018, provisional application No. 62/627,464, filed
(Continued)

(51) Int. Cl.
*A61B 6/00* (2006.01)
*G01T 1/20* (2006.01)
(Continued)

(52) U.S. Cl.
CPC .............. *A61B 6/4405* (2013.01); *A61B 6/06* (2013.01); *A61B 6/107* (2013.01); *A61B 6/405* (2013.01); *A61B 6/4441* (2013.01); *A61B 6/467* (2013.01); *A61B 6/487* (2013.01); *A61B 6/54* (2013.01); *A61B 6/56* (2013.01); *G01T 1/20* (2013.01); *G01T 1/2002* (2013.01);
(Continued)

(58) Field of Classification Search
None
See application file for complete search history.

(56) References Cited

U.S. PATENT DOCUMENTS

| 4,856,036 A | 8/1989 | Malcolm |
| 5,784,434 A | 7/1998 | Shieh |

(Continued)

FOREIGN PATENT DOCUMENTS

| JP | 2003279500 | 10/2003 |
| WO | 2005081956 A2 | 9/2005 |

(Continued)

OTHER PUBLICATIONS

CMOS X-Ray Detectors for Industrial Non-Destructive Testing, Teledyne Dalsa Industrial X-Ray Detectors X-Ray Solutions for Non-Destructive Testing, Teledyne Dalsa.
(Continued)

*Primary Examiner* — Hook K Song
(74) *Attorney, Agent, or Firm* — McAndrews, Held & Malloy, Ltd.

(57) ABSTRACT

Radiography backscatter shields and X-ray imaging systems including backscatter shields are disclosed. An example X-ray backscatter shield includes: a conforming backscatter shield configured to provide shielding from Compton scatter radiation when placed in contact with an object to be scanned; and a shield frame configured to couple the backscatter shield to an X-ray source.

10 Claims, 12 Drawing Sheets

Related U.S. Application Data on Feb. 7, 2018, provisional application No. 62/627,473, filed on Feb. 7, 2018, provisional application No. 62/627,469, filed on Feb. 7, 2018.

(51) Int. Cl.

| | |
|---|---|
| *H01J 35/02* | (2006.01) |
| *G01T 7/00* | (2006.01) |
| *A61B 6/06* | (2006.01) |
| *G01T 1/24* | (2006.01) |
| *H04N 5/321* | (2006.01) |
| *A61B 6/10* | (2006.01) |
| *G21F 1/08* | (2006.01) |

(52) U.S. Cl.
CPC .............. *G01T 1/2018* (2013.01); *G01T 1/24* (2013.01); *G01T 7/00* (2013.01); *G21F 1/085* (2013.01); *H01J 35/02* (2013.01); *H04N 5/321* (2013.01); *A61B 6/4035* (2013.01)

(56) References Cited

U.S. PATENT DOCUMENTS

| | | | | |
|---|---|---|---|---|
| 6,064,715 | A | 5/2000 | Sklebitz | |
| 6,543,936 | B2* | 4/2003 | Feldman | A61B 6/145 378/191 |
| 7,289,601 | B2 | 10/2007 | Caseault | |
| 7,289,602 | B1 | 10/2007 | Polichar | |
| 8,023,722 | B1 | 9/2011 | Kovarik | |
| 9,883,840 | B2 | 2/2018 | Barbato | |
| 2002/0031203 | A1 | 3/2002 | Polichar | |
| 2008/0020332 | A1 | 1/2008 | Lavenda | |
| 2009/0016490 | A1 | 1/2009 | Campbell | |
| 2012/0033788 | A1 | 2/2012 | Kovarik | |
| 2012/0148031 | A1 | 6/2012 | Eaves | |
| 2013/0003923 | A1* | 1/2013 | Sackett | G01N 23/223 378/44 |
| 2013/0195248 | A1 | 8/2013 | Rothschild | |
| 2016/0174915 | A1 | 6/2016 | O'Dea | |
| 2017/0245827 | A1* | 8/2017 | Joshi | A61B 6/542 |
| 2018/0153487 | A1 | 6/2018 | Eaves | |
| 2020/0054294 | A1* | 2/2020 | Belson | A61B 6/4441 |

FOREIGN PATENT DOCUMENTS

| | | |
|---|---|---|
| WO | 2005081956 A3 | 9/2005 |
| WO | 2014022217 | 2/2014 |
| WO | 2016172611 | 10/2016 |

OTHER PUBLICATIONS

CMOSXRAY: "OpenVision LT Video RevA", YouTube, Jan. 20, 2011, p. 1, XP054979294, Retrieved from the Internet: URL:https://www.youtube.com/watch?v=ovU5I7D4ztM [retrieved on Apr. 10, 2019].

EOD Training with Vidisco, The Slovakian EOD Training School Plays it Safe with Vidisco, An interview with a Commander at the Slovakian EOD School by Rachel Lieberman.

Go-Scan Portable Digital X-Ray Solution for NDT, Teledyne ICM.

Int'l Search Report and Written Opinion Appln. No. PCT/US2019/017041 dated May 7, 2019.

Int'l Search Report and Written Opinion Appln. No. PCT/US2019/017047 dated May 7, 2019.

Int'l Search Report and Written Opinion Appln. No. PCT/US2019/017051 dated May 7, 2019.

Int'l Search Report and Written Opinion Appln. No. PCT/US2019/017053 dated May 13, 2019.

MXR—Modular X-ray Robotic Scanner, © 2008-2016 Smart Imaging Systems Inc.

Portable X-Ray Generators, CP120B & CP160B, Constant potential ultralightweight battery powered X-ray generators for NDT and Security inspections, www.icmxray.com/ndt.

X-ray Sources, 60kV & 70kV 12W MAGPRO® Data Sheet, Tub-Data-1018, Rev B, Copyright © 2016, Moxtek.

Xplus SecurityRobot, Copyright 2015 Visiconsult GmbH.

The LIXI Profiler for Pipe Inspection https://lixi.com/lixi-profiler/ (archived Oct. 28, 2016.

* cited by examiner

RADIOGRAPHY BACKSCATTER SHIELDS AND X-RAY IMAGING SYSTEMS INCLUDING BACKSCATTER SHIELDS

RELATED APPLICATIONS

This patent claims priority to U.S. Provisional Patent Application Ser. No. 62/627,473, filed Feb. 7, 2018, entitled "X-Ray Detectors for Generating Digital Images," U.S. Provisional Patent Application Ser. No. 62/627,469, filed Feb. 7, 2018, entitled "Systems and Methods for Digital X-Ray Imaging," U.S. Provisional Patent Application Ser. No. 62/627,464, filed Feb. 7, 2018, entitled "Systems and Methods for Digital X-Ray Imaging," and U.S. Provisional Patent Application Ser. No. 62/627,466, filed Feb. 7, 2018, entitled "Radiography Backscatter Shields and X-Ray Imaging Systems Including Backscatter Shields." The entireties of U.S. Provisional Patent Application Ser. No. 62/627,473, U.S. Provisional Patent Application Ser. No. 62/627,469, U.S. Provisional Patent Application Ser. No. 62/627,464, and U.S. Provisional Patent Application Ser. No. 62/627,466 are incorporated herein by reference.

BACKGROUND

This disclosure relates generally to radiography, and more particularly, to radiography backscatter shields and X-ray imaging systems including backscatter shields.

SUMMARY

Radiography backscatter shields and X-ray imaging systems including backscatter shields are disclosed, substantially as illustrated by and described in connection with at least one of the figures, as set forth more completely in the claims.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

The figures are not necessarily to scale. Wherever appropriate, similar or identical reference numerals are used to refer to similar or identical components.

DETAILED DESCRIPTION

Figure 1:
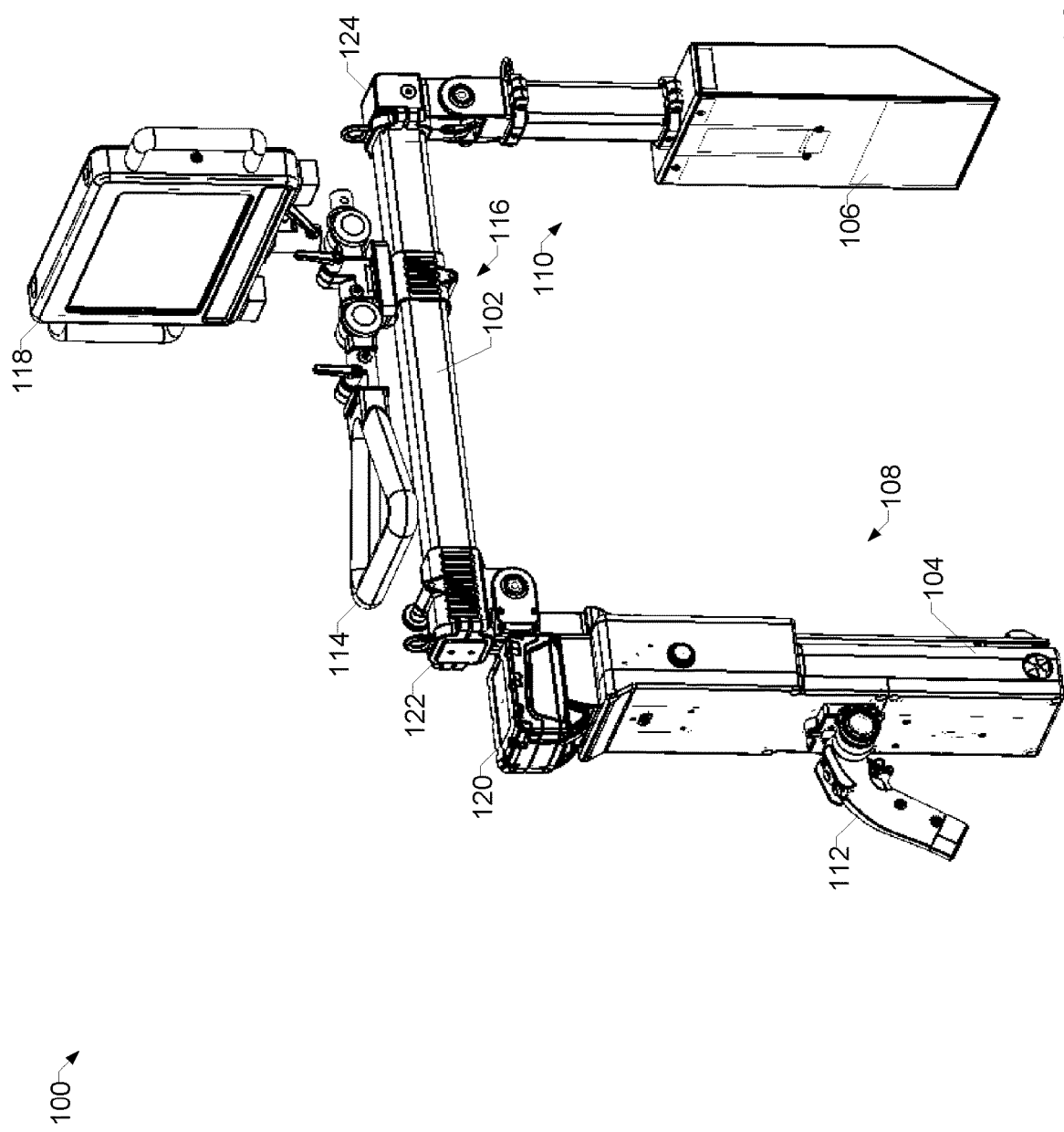
FIG. 1 is a perspective view of an example handheld X-ray imaging system to generate and output digital images and/or video based on incident X-rays, in accordance with aspects of this disclosure.

Disclosed example backscatter shielding devices for handheld X-ray imaging equipment reduce the radiation dosage to the operator caused by radiation scattering back from the scanned object. Disclosed backscatter shields include conforming shielding material to enable the backscatter shield to make close contact with the object to be radiographically scanned or tested. The contours of the shielding material may be tailored to the contours of the object being tested.

In some examples, a backscatter shielding device includes a triggering device for a complementary switch on the imaging equipment. The triggering device, when detected by the switch, enables operation of the imaging equipment. Thus, disclosed examples ensure proper installation of the backscatter shielding device prior to use of the imaging equipment, which improves operator safety by reducing the radiation dose to the operator.

As used herein, the term "real-time" refers to the actual time elapsed in the performance of a computation by a computing device, the result of the computation being required for the continuation of a physical process (i.e., no significant delays are introduced). For example, real-time display of captured images includes processing captured image data and displaying the resulting output images to create the perception to a user that the images are displayed immediately upon capture. As used herein, the term "portable" includes handheld (e.g., capable of being carried and operated by a single person) and/or wheeled (e.g., capable of being transported and operated while wheels are attached and/or placed on wheels).

Disclosed example backscatter shielding devices include: a conforming backscatter shield configured to provide shielding from Compton scatter radiation when placed in contact with an object to be scanned; and a shield frame configured to couple the backscatter shield to an X-ray source.

In some examples, the backscatter shield includes a first end and a second end having a contour corresponding to an outer surface of the object to be scanned. In some examples, the backscatter shield includes silicone blended with a shielding material. In some examples, the shielding material is at least one of bismuth, tungsten, lead or iron.

In some examples, the X-ray shield includes a plate embedded within the backscatter shield, the plate configured to attach the backscatter shield to the shield frame. In some examples, the plate is configured to detachably attach the backscatter shield to the shield frame. In some examples, the shield frame includes an X-ray source attachment rail configured to mount the shield frame to the X-ray source, and a switch actuator configured to activate a switch in the X-ray source when the shield frame is fully mounted to the X-ray source. In some examples, the switch includes at least one of a mechanical switch, a capacitive sensor, an inductive sensor, a magnetic sensor, or an optical sensor.

Disclosed example portable X-ray scanners, include: an X-ray detector configured to generate images based on incident X-ray radiation; an X-ray tube configured to output X-ray radiation; and a frame configured to: hold the X-ray detector; hold the X-ray tube such that the X-ray tube directs the X-ray radiation to the X-ray detector; and enable attachment of a Compton scatter shielding device to the frame.

Some example portable X-ray scanners further include a switch configured to detect attachment of the shielding device to the frame and enable activation of the X-ray tube in response to detecting the attachment of the shielding device. Some examples further include a collimator configured to filter the output of the X-ray radiation, in which the switch is configured to detect attachment of the shielding device adjacent the collimator. In some examples, the switch includes a sensor configured to detect the presence of the shielding device. In some examples, the sensor iat least one of a mechanical switch, a capacitive sensor, an inductive sensor, a magnetic sensor, or an optical sensor.

In some examples, the switch is configured to enable activation of the X-ray tube based on whether the X-ray tube is configured to use a tube voltage that satisfies a threshold tube voltage. In some examples, the threshold tube voltage is 70 kV, and the switch is configured to disable the X-ray tube when the X-ray tube is configured to use at least the threshold tube voltage and attachment of the shielding device to the frame is not detected. In some examples, the frame includes an attachment rail configured to hold the shielding device.

Disclosed example portable X-ray scanners include: an X-ray detector configured to generate images based on incident X-ray radiation; an X-ray tube configured to output X-ray radiation; and a frame configured to: hold the X-ray detector; hold the X-ray tube such that the X-ray tube directs the X-ray radiation to the X-ray detector; and a backscatter shield configured to provide shielding from Compton scatter radiation when placed in contact with an object to be scanned.

Disclosed example X-ray scanners further include a switch configured to detect attachment of the backscatter shield to the frame and enable activation of the X-ray tube in response to detecting the attachment of the backscatter shield. In some examples, the switch is configured to enable activation of the X-ray tube based on whether the X-ray tube is configured to use a tube voltage that satisfies a threshold tube voltage. In some examples, the threshold tube voltage is 70 kV, and the switch is configured to disable the X-ray tube when the X-ray tube is configured to use at least the threshold tube voltage and attachment of the shielding device to the frame is not detected.

FIG. 1 is a perspective view of an example handheld X-ray imaging system 100 to generate and output digital images and/or video based on incident X-rays. The example handheld X-ray imaging system 100 may be used to perform non-destructive testing (NDT), medical scanning, security scanning, and/or any other scanning application.

The system 100 of FIG. 1 includes a frame 102 that holds an X-ray generator 104 and an X-ray detector 106. In the example of FIG. 1, the frame 102 is C-shaped, such that the X-ray generator 104 directs X-ray radiation toward the X-ray detector 106. As described in more detail below, the frame 102 is positionable (e.g., held by an operator, supported by an external support structure and/or manipulated by the operator, etc.) around an object to be scanned with X-rays. The example frame 102 is constructed using carbon fiber and/or machined aluminum.

The X-ray generator 104 is located on a first section 108 of the C-shaped frame 102 generates and outputs X-ray radiation, which traverses and/or scatters based on the state of the object under test. The X-ray detector 106 is located on a second section 110 of the frame 102 (e.g., opposite the first section 108) and receives incident radiation generated by the X-ray generator 104.

The example frame 102 may be manipulated using one or more handles 112, 114. A first one of the handles 112 is an operator control handle, and enables an operator to both mechanically manipulate the frame 102 and control the operation of the handheld X-ray imaging system 100. A second one of the handles 114 is adjustable and may be secured to provide the operator with leverage to manipulate the frame 102. The example handle 114 may be oriented with multiple degrees of freedom and/or adjusted along a length of a central section 116 of the frame 102.

During operation, the handheld X-ray imaging system 100 generates digital images (e.g., digital video and/or digital still images) from the X-ray radiation. The handheld X-ray imaging system 100 may store the digital images on one or more storage devices, display the digital images on a display device 118, and/or transmit the digital images to a remote receiver. The example display device 118 is attachable to the example frame 102 and/or may be oriented for viewing by the operator. The display device 118 may also be detached from the frame 102. When detached, the display device 118 receives the digital images (e.g., still images and/or video) via a wireless data connection. When attached, the display device 118 may receive the digital images via a wired connection and/or a wireless connection.

A power supply 120, such as a detachable battery, is attached to the frame 102 and provides power to the X-ray generator 104, the X-ray detector 106, and/or other circuitry of the handheld X-ray imaging system 100. An example power supply 120 that may be used is a lithium-ion battery pack. The display device 118 may receive power from the power supply 120 and/or from another power source such as an internal battery of the display device 118.

The example central section 116 of the frame 102 is coupled to the first section 108 via a joint 122 and to the second section 110 via a joint 124. The example joints 122, 124 are hollow to facilitate routing of cabling between the sections 108, 110, 116. The joints 122, 124 enable the first section 108 and the second section 110 to be folded toward the center section to further improve the compactness of the handheld X-ray imaging system 100 when not in use (e.g., during storage and/or travel).

Figure 2:
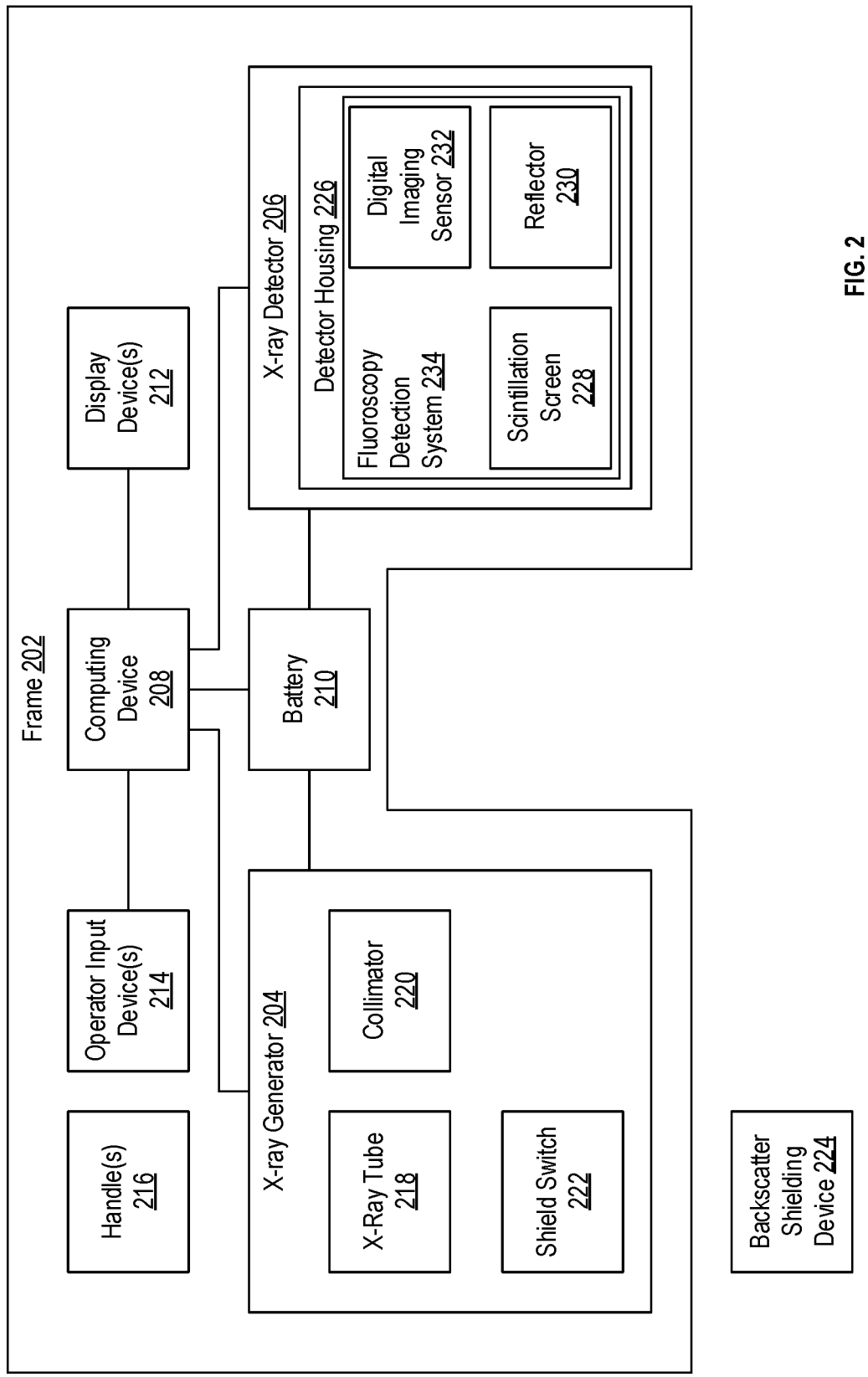
FIG. 2 is a block diagram of the example handheld X-ray imaging system of FIG. 1.

FIG. 2 is a block diagram of an example digital X-ray imaging system 200 that may be used to implement the handheld X-ray imaging system 100 of FIG. 1. The example digital X-ray imaging system 200 of FIG. 2 includes a frame 202 holding an X-ray generator 204, an X-ray detector 206, a computing device 208, a battery 210, one or more display device(s) 212, one or more operator input device(s) 214, and one or more handle(s) 216.

The X-ray generator 204 includes an X-ray tube 218, a collimator 220, and a shield switch 222. The X-ray tube 218 generates X-rays when energized. In some examples, the X-ray tube 218 operates at voltages between 40 kV and 120 kV. In combination with a shielding device, X-ray tube voltages between 70 kV and 120 kV may be used while staying within acceptable X-ray dosage limits for the operator. Other voltage ranges may also be used.

The collimator 220 filters the X-ray radiation output by the X-ray tube 218 to more narrowly direct the X-ray radiation at the X-ray detector 206 and any intervening objects. The collimator 220 reduces the X-ray dose to the operator of the system 200, reduces undesired X-ray energies to the detector 206 resulting from X-ray scattering, and/or improves the resulting digital image generated at the X-ray detector 206.

The shield switch 222 selectively enables and/or disables the X-ray tube 218 based on whether a backscatter shielding device 224 is attached to the frame. The backscatter shielding device 224 reduces the dose to the operator holding the frame 202 by providing shielding between the collimator 220 and an object under test. The example backscatter shielding device 224 includes a switch trigger configured to trigger the shield switch 222 when properly installed. For example, the shield switch 222 may be a reed switch or similar magnetically-triggered switch, and the backscatter shielding device 224 includes a magnet. The reed switch and magnet are respectively positioned on the frame 202 and the backscatter shielding device 224 such that the magnet triggers the reed switch when the backscatter shielding device 224 is attached to the frame 202. The shield switch 222 may include any type of a capacitive sensor, an inductive sensor, a magnetic sensor, an optical sensor, and/or any other type of proximity sensor.

The shield switch 222 is configured to disable the X-ray tube 218 when the backscatter shielding device 224 is not installed. The shield switch 222 may be implemented using, for example, hardware circuitry and/or via software executed by the computing device 208. In some examples, the computing device 208 may selectively override the shield switch 222 to permit operation of the X-ray tube 218 when the backscatter shielding device 224 is not installed. The override may be controlled by an administrator or other authorized user.

The X-ray detector 206 of FIG. 2 generates digital images based on incident X-ray radiation (e.g., generated by the X-ray tube 218 and directed toward the X-ray detector 206 by the collimator 220). The example X-ray detector 206 includes a detector housing 226, which holds a scintillation screen 228, a reflector 230, and a digital imaging sensor 232. The scintillation screen 228, the reflector 230, and the digital imaging sensor 232 are components of a fluoroscopy detection system 234. The example fluoroscopy detection system 234 is configured so that the digital imaging sensor 232 (e.g., a camera, a sensor chip, etc.) receives the image indirectly via the scintillation screen 228 and the reflector 230. In other examples, the fluoroscopy detection system 234 includes a sensor panel (e.g., a CCD panel, a CMOS panel, etc.) configured to receive the X-rays directly, and to generate the digital images.

In some other examples, the scintillation screen 228, may be replaced with a solid state panel that is coupled to the scintillation screen 228 and has pixels that correspond to portions of the scintillation screen 228. Example solid state panels may include CMOS X-ray panels and/or CCD X-ray panels.

The computing device 208 controls the X-ray tube 218, receives digital images from the X-ray detector 206 (e.g., from the digital imaging sensor 232), and outputs the digital images to the display device 212. Additionally or alternatively, the computing device 208 may store digital images to a storage device. The computing device 208 may output the digital images as digital video to aid in real-time non-destructive testing and/or store digital still images.

As mentioned above, the computing device 208 may provide the digital images to the display device(s) 212 via a wired connection or a wireless connection. To this end, the computing device 208 includes wireless communication circuitry. For example, the display device(s) 212 may be detachable from the frame 202 and held separately from the frame 202 while the computing device 208 wirelessly transmits the digital images to the display device(s) 212. The display device(s) 212 may include a smartphone, a tablet computer, a laptop computer, a wireless monitoring device, and/or any other type of display device equipped with wired and/or wireless communications circuitry to communicate with (e.g., receive digital images from) the computing device 208.

In some examples, the computing device 208 adds data to the digital images to assist in subsequent analysis of the digital images. Example data includes a timestamp, a date stamp, geographic data, or a scanner inclination. The example computing device 208 adds the data to the images by adding metadata to the digital image file(s) and/or by superimposing a visual representation of the data onto a portion of the digital images.

The operator input device(s) 214 enable the operator to configure and/or control the example digital X-ray imaging system 200. For example, the operator input device(s) 214 may provide input to the computing device 208, which controls operation and/or configures the settings of the digital X-ray imaging system 200. Example operator input device(s) 214 include a trigger (e.g., for controlling activation of the X-ray tube 218), buttons, switches, analog joysticks, thumbpads, trackballs, and/or any other type of user input device.

The handle(s) 216 are attached to the frame 202 and enable physical control and manipulation of the frame 202, the X-ray generator 204, and the X-ray detector 206. In some examples, one or more of the operator input device(s) 214 are implemented on the handle(s) 216 to enable a user to both physically manipulate and control operation of the digital X-ray imaging system 200.

Figure 3A:
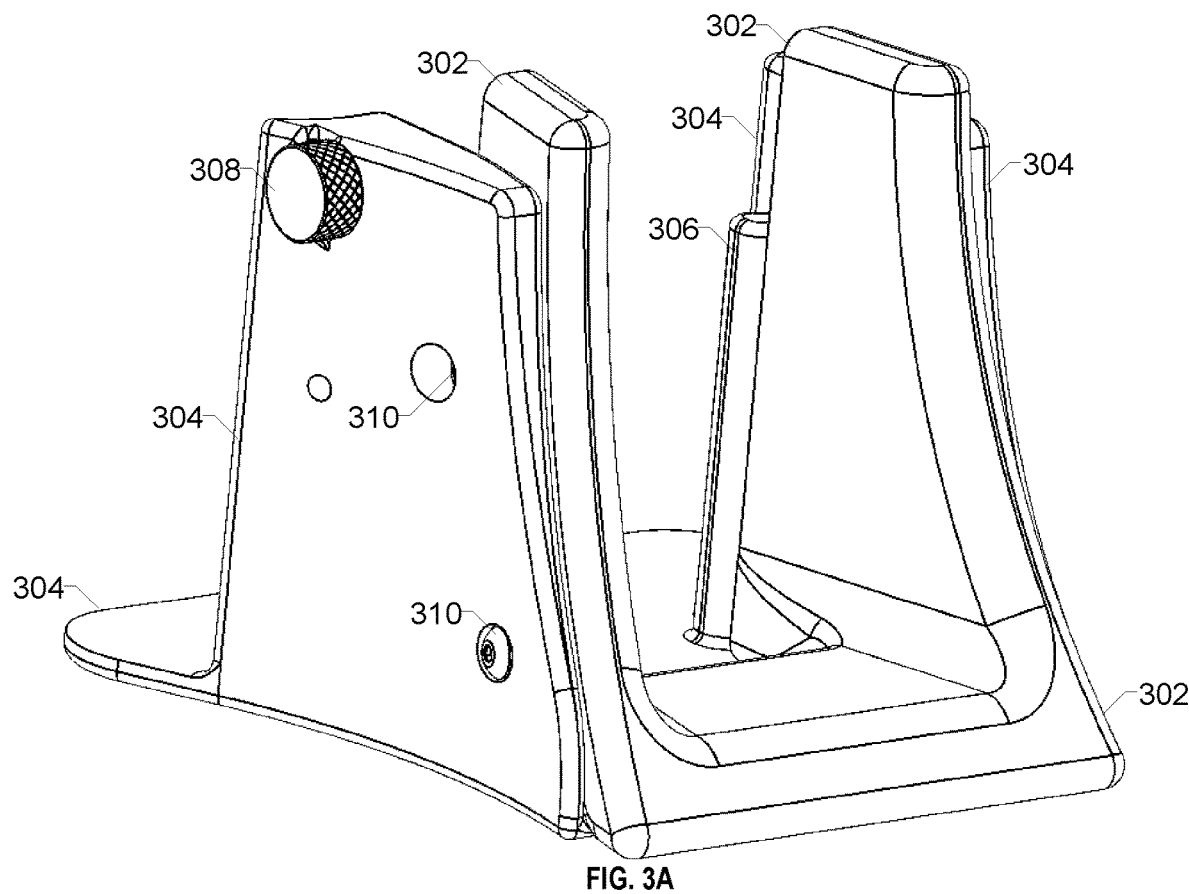
FIGS. 3A-3G are views of an example implementation of a backscatter shielding device to provide shielding against Compton scatter during handheld radiography.
Figure 3B:
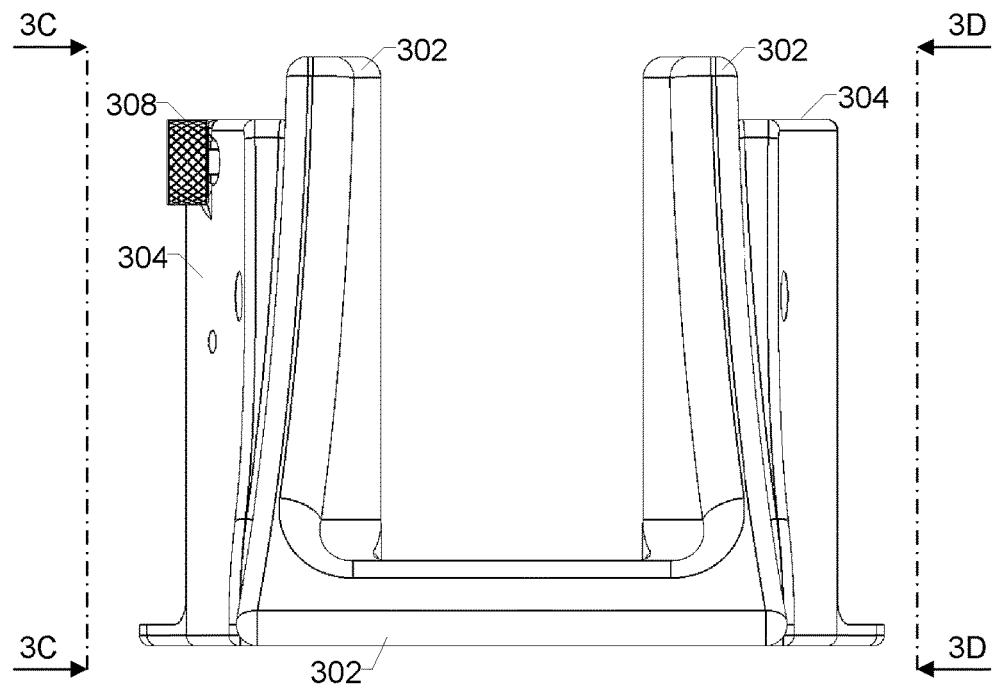
Figure 3C:
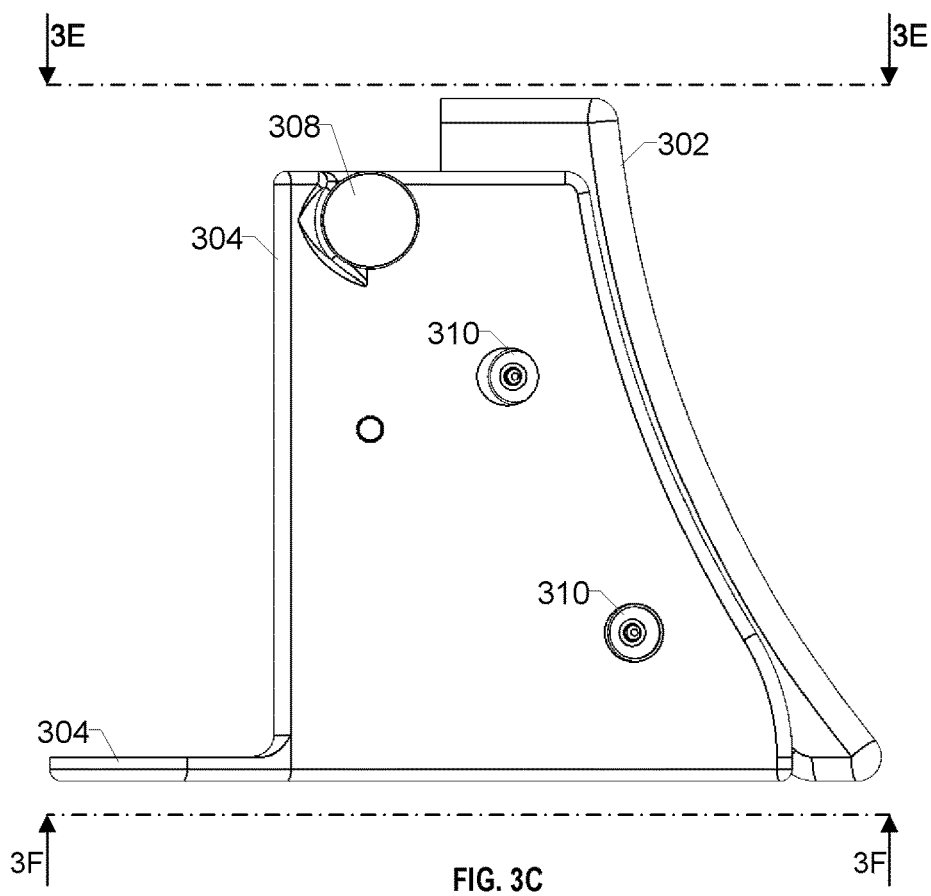
Figure 3D:
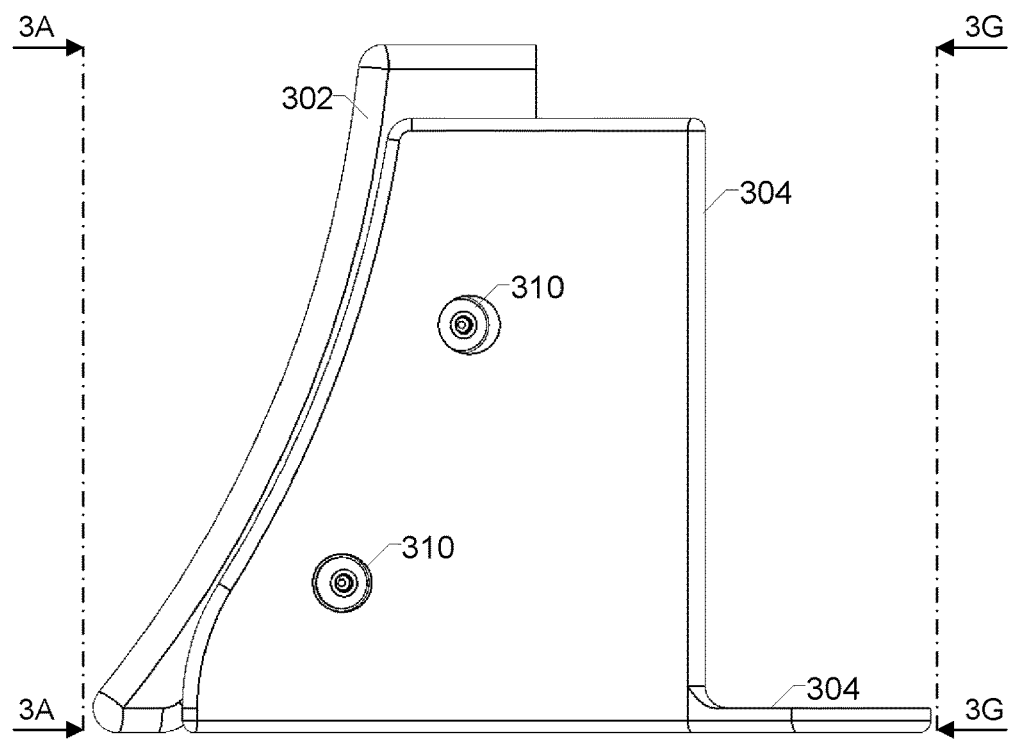
Figure 3E:
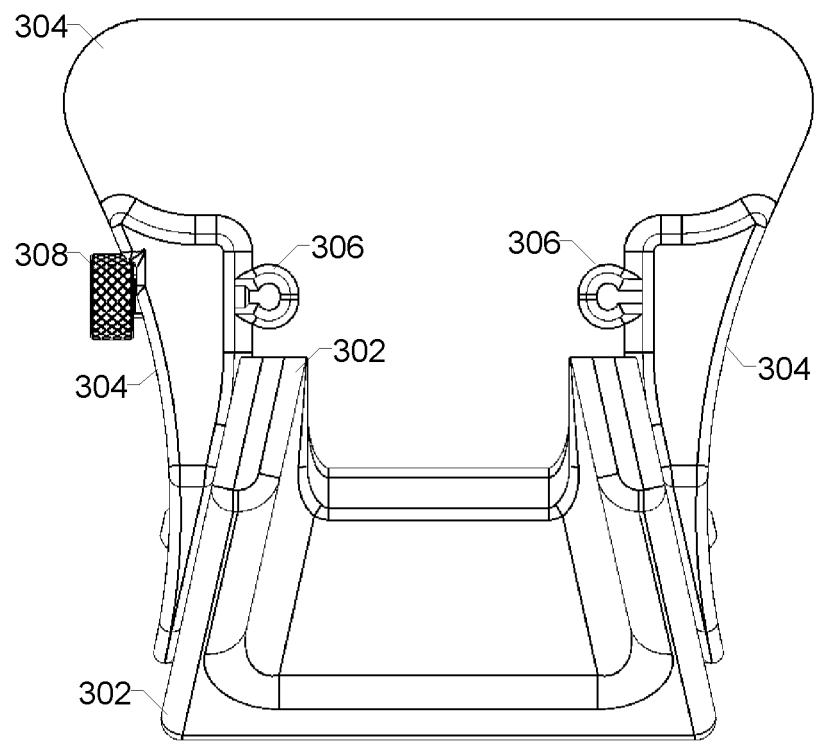
Figure 3F:
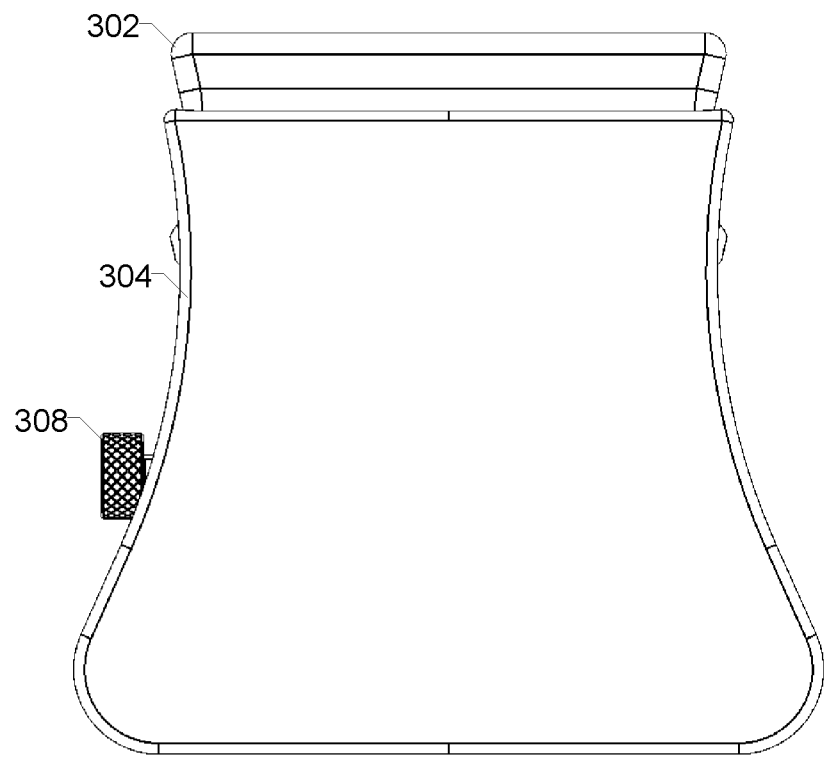
Figure 3G:
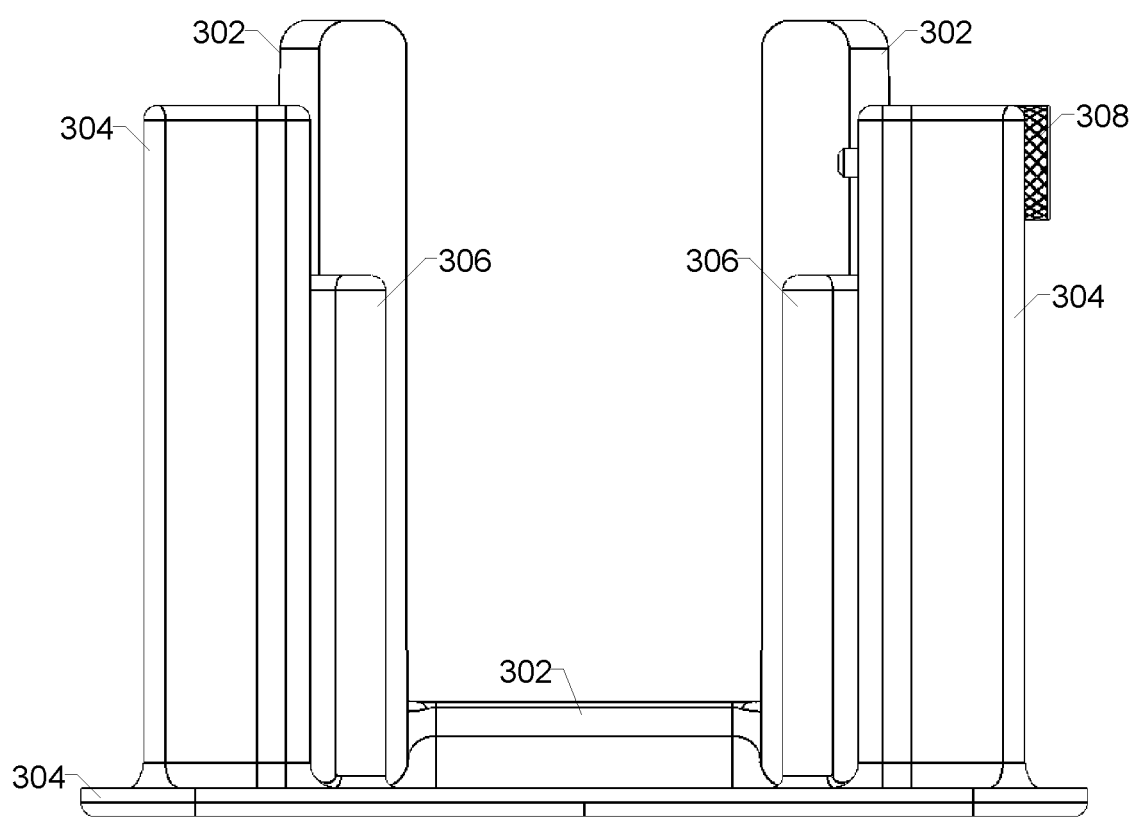

FIG. 3A is a perspective view of an example backscatter shielding device 300 to provide shielding against backscatter during handheld radiography. The example backscatter shielding device 300 may implement the backscatter shielding device 224 in the system 200 of FIG. 2. FIG. 3B is a front elevation view of the backscatter shielding device 300. FIG. 3C is a left-side elevation view of the backscatter shielding device 300, and FIG. 3D is a right-side elevation view of the backscatter shield. FIG. 3E is a top plan view of the backscatter shielding device 300, and FIG. 3F is a bottom plan view of the backscatter shielding device 300. FIG. 3G is a rear elevation view of the backscatter shielding device 300.

The example backscatter shielding device 300 includes a conforming backscatter shield 302 and a shield frame 304. The backscatter shield 302 provides shielding from Compton scatter radiation when placed in contact with an object to be scanned. The shield frame 304 couples the backscatter shield 302 to the X-ray source (e.g., to the frame 102 holding the X-ray generator 104).

The example backscatter shield 302 of FIG. 3A-3G at least partially conforms to a surface of the object to be scanned (e.g., on a first end of the backscatter shield 302) and/or to a portion of the frame 102 when installed (e.g., on a second end of the backscatter shield 302). The conformance by the backscatter shield 302 improves the shielding by reducing or eliminating gaps between the object to be scanned and the shield 302. In the illustrated example, the backscatter shield 302 has a curved or contoured surface on the second end to conformably engage a corresponding curved or contoured surface of the object.

To couple the shield frame 304 to the frame 102, the example shield frame 304 includes rail slides 306, which fit within respective rail slots of the frame 102. A spring-loaded plunger 308 enables the shield frame 304 to be secured to the frame 102. The shield frame 304 includes a switch actuator (e.g., a magnet) to indicate to the shield switch 222 (e.g., a reed switch) that the backscatter shielding device 300 is properly installed. The switch actuator may be positioned at any appropriate location, in or on the backscatter shield 302 and/or the frame 304, where the backscatter shield 302 or the shield frame 304 is adjacent the frame 102 in a fully installed position. The shield switch 222 and the switch actuator are installed in complementary locations in the frame 102 and the shield frame 304 and/or the backscatter shield 302.

The example backscatter shield 302 of FIG. 3 includes silicone blended with a shielding material. The shielding material may include bismuth, tungsten, lead and/or iron, and/or any other radiation shielding material. The example silicone is a high-wear blend, such as silicone 940. To facilitate coupling of the backscatter shield 302 to the shield frame 304, the example backscatter shield 302 includes plates embedded within the backscatter shield 302. The plates may be screwed, bolted, or otherwise attached to the shield frame 304. Example screws 310 to couple the backscatter shield 302 to the shield frame 304 are illustrated. Additionally or alternatively, the backscatter shield 302 may be attached to the shield frame 304 via adhesives such as glue or epoxy.

Figure 4:
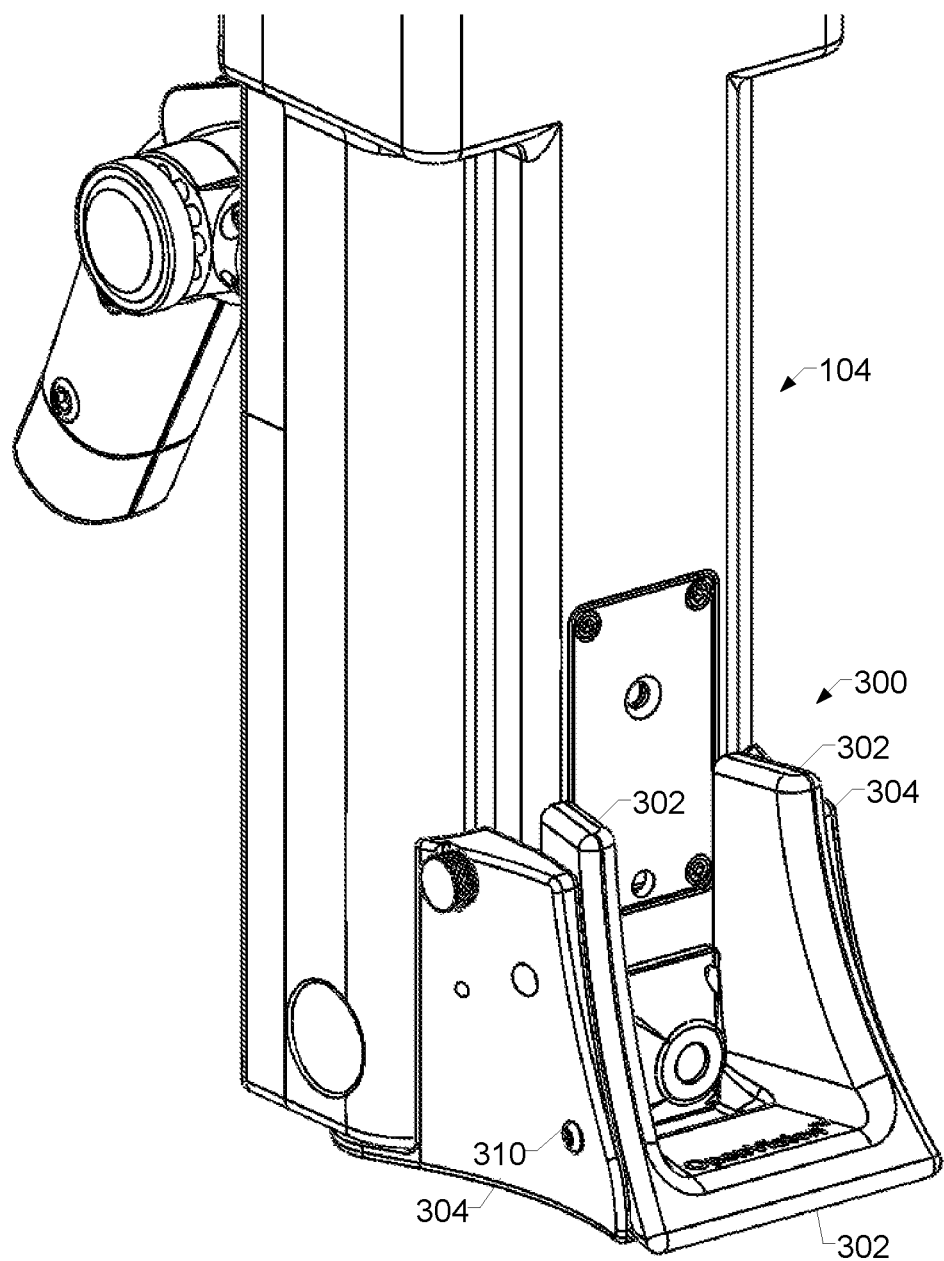
FIG. 4 illustrates the example shielding device of FIG. 3 installed on the example handheld X-ray imaging system of FIG. 1.
Figure 5:
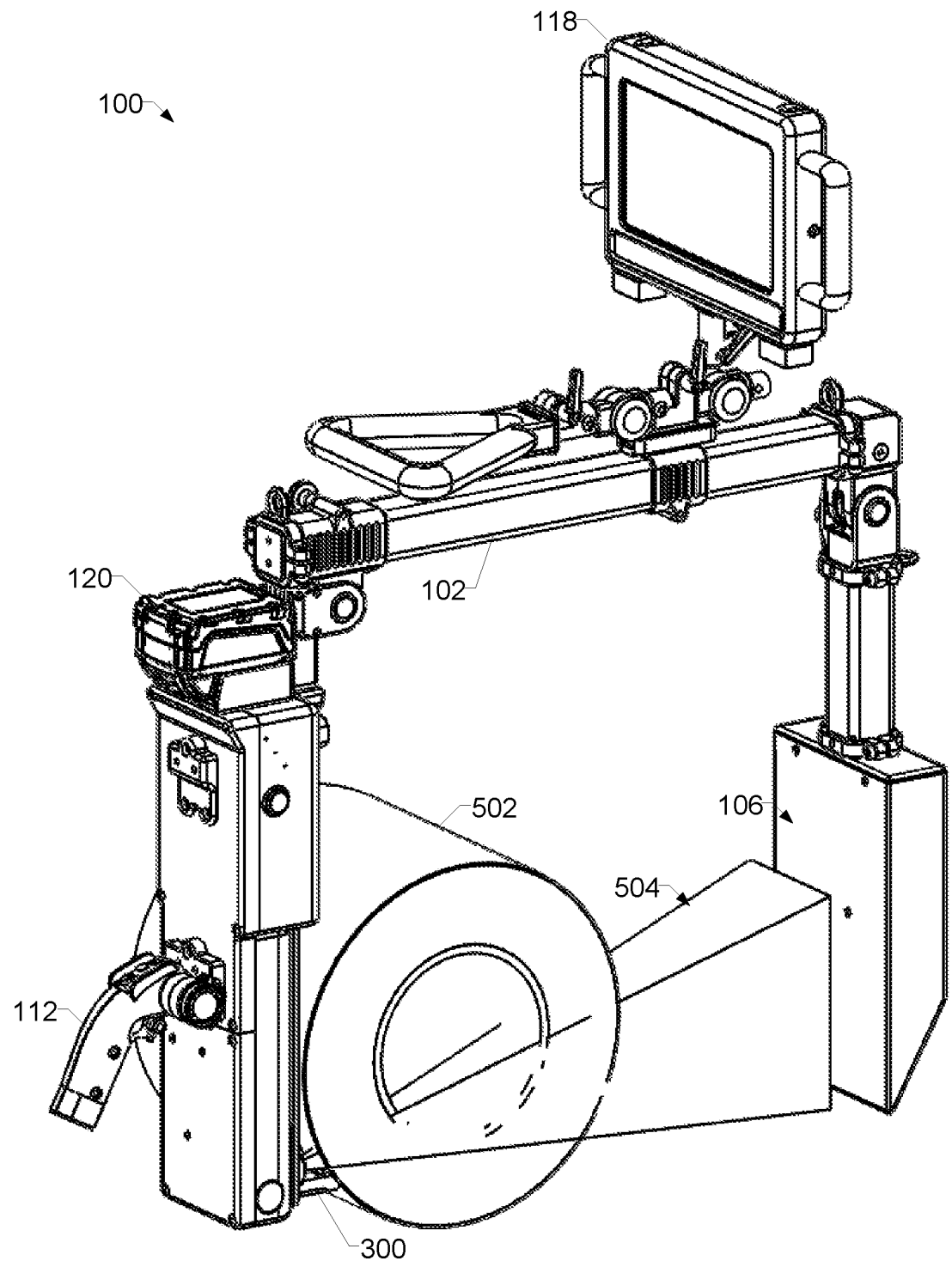
FIG. 5 illustrates the example handheld X-ray imaging system, with the backscatter shield of FIG. 3 installed, during imaging of an object under test.

FIG. 4 illustrates the example backscatter shielding device 300 of FIG. 3 installed on the example handheld X-ray imaging system of FIG. 1. FIG. 5 illustrates the example handheld X-ray imaging system of FIG. 1, with the backscatter shielding device 300 of FIG. 3 installed, during imaging of an object under test 502 by directing X-rays 504 from the X-ray tube 218 to the X-ray detector 106.

The backscatter shielding device 300 is installed on the frame 102 by sliding the rail slides 306 into corresponding rails on the frame 102, until a stop surface (e.g., the bottom of the shield frame 304) meets a stop surface on the frame 102. Other techniques of reliably positioning the backscatter shielding device 300 may be used.

As mentioned above, the collimator 220 reduces X-ray radiation that is not directed at the X-ray detector 106, so the concentration of the X-ray radiation 504 that is not scattered by the object 502 is incident on the X-ray detector 106.

The backscatter shielding device 300 conforms to the object 502 such that the backscatter shielding device 300 and the object 502 enclose and/or shield backscattered Compton scatter radiation. For example, the backscatter shield 302 conforms to the surface of the object 502, and the object contacts or nearly contacts the frame 102. The example backscatter shield 302 is positioned in the primary pathways for Compton scatter radiation to reach an operator, thereby substantially reducing the Compton scatter dose received by the operator and/or increasing the power that may be used to drive the X-ray tube 218.

Figure 6:
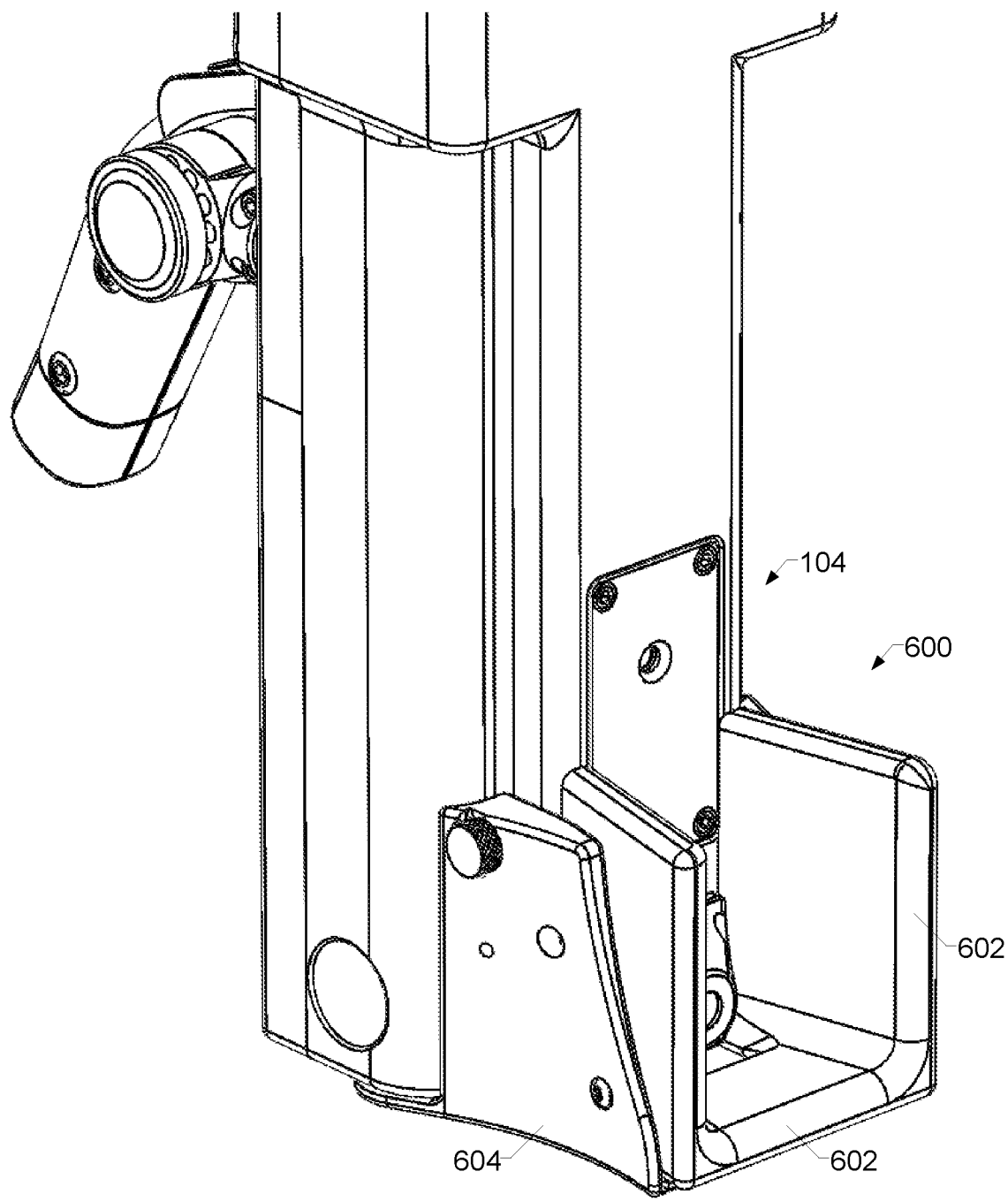
FIG. 6 illustrates another example backscatter shield installed on the example handheld X-ray imaging system of FIG. 1.

FIG. 6 illustrates another example backscatter shielding device 600 installed on the example handheld X-ray imaging system 100 of FIG. 1. The example backscatter shielding device 600 is substantially identical to the backscatter shielding device 300 of FIGS. 3A-3G, 4, and 5, except that the backscatter shielding device 600 is configured to more closely conform to flat objects than to curved objects as with the backscatter shielding device 300.

To this end, the backscatter shielding device 600 includes an backscatter shield 602 and a shield frame 604. The shield frame 604 is identical to the example shield frame 304 and/or may be implemented as in any of the examples described above with reference to the shield frame 304. The backscatter shield 602 is also identical to the example backscatter shield 302, with the exception of the contour of the end making contact with the object. As mentioned above, the backscatter shield 602 has a flat contour to better conform to flat objects.

Figure 7:
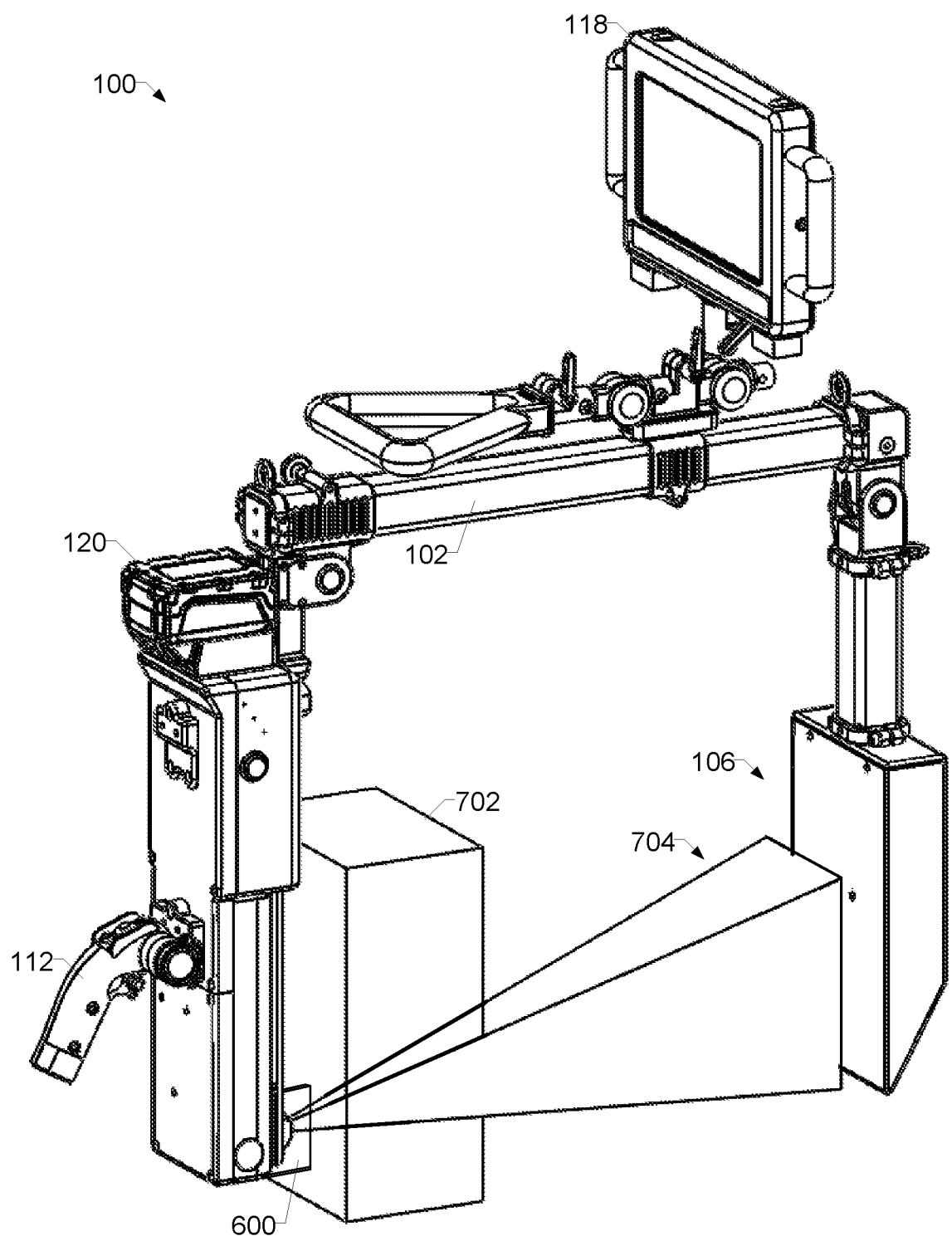
FIG. 7 illustrates the example handheld X-ray imaging system, with the backscatter shield of FIG. 6 installed, during imaging of another example object under test.

FIG. 7 illustrates the example handheld X-ray imaging system 100 of FIG. 1, with the backscatter shield 600 of FIG. 6 installed, during imaging of another example object under test 702 by directing X-rays 704 from the X-ray tube 218 to the X-ray detector 106.

Figure 8:
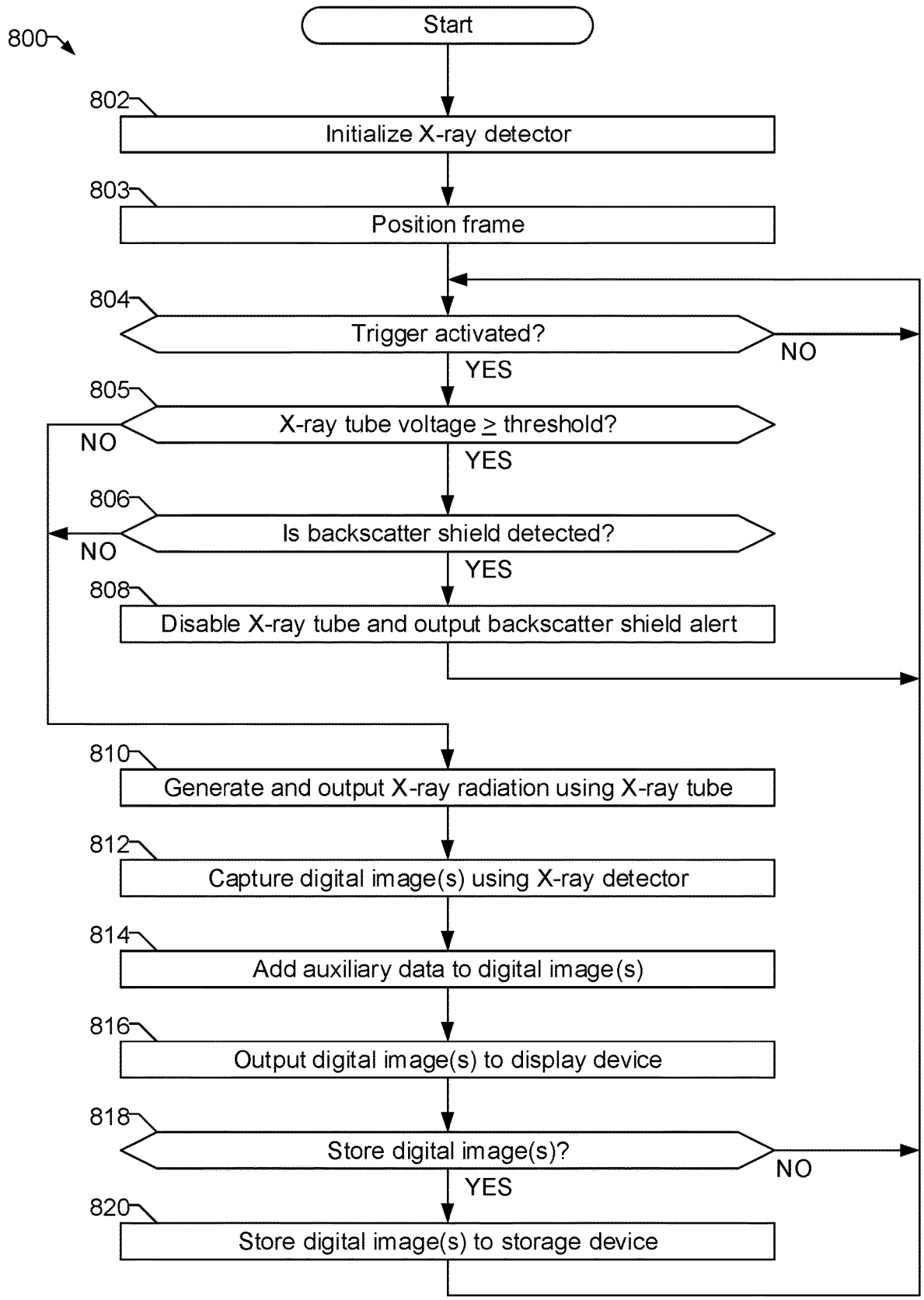
FIG. 8 is a flowchart representative of example machine readable instructions which may be executed by the example computing device of FIG. 2 to perform digital X-ray imaging, in accordance with aspects of this disclosure.

FIG. 8 is a flowchart representative of example machine readable instructions 800 which may be executed by the example computing device 208 of FIG. 2 to perform digital X-ray imaging. The example machine readable instructions 800 of FIG. 8 are described below with reference to the digital X-ray imaging system 200 of FIG. 2, but may be performed by the digital X-ray imaging system 100 of FIG. 1.

At block 802, the example computing device 208 initializes the X-ray detector 206. For example, the computing device 208 may verify that the X-ray detector 206 is in communication with the computing device 208 and/or is configured to capture digital images of X-ray radiation. At block 803, an operator of the digital X-ray imaging system 200 may position the frame 202 adjacent on object under test, such that the object under test is located between the X-ray detector 206 and the X-ray tube 218.

At block 804, the computing device 208 determines whether a trigger is activated. For example, the computing device 208 may activate the X-ray tube 218 in response to activation of a trigger (e.g., a physical trigger, a button, a switch, etc.) by an operator. If the trigger has not been activated (block 804), control returns to block 804 to await activation of the trigger.

When the trigger is activated (block 804), at block 805 the computing device 208 determines whether the X-ray tube voltage is at least a threshold voltage. An example threshold is 70 kV. For example, the X-ray tube voltage may be configured to be between 70 kV and 120 kV, in which case the computing device 208 requires the backscatter shielding device 224 to be detected (e.g., via the shield switch 222).

If the X-ray tube voltage is at least the threshold (block 805), at block 806 the computing device 208 determines whether a backscatter shield is detected. For example, the computing device 208 may determine whether the backscatter shield (e.g., the backscatter shielding device 224, the backscatter shielding device 300, the backscatter shield 600) is installed using the shield switch 222. If the backscatter shield is not detected (block 806), at block 808 the computing device 208 disables the X-ray tube 218 and outputs a backscatter shield alert (e.g., via a visual and/or audible alarm, via the display device 212, etc.). Control then returns to block 804.

If the backscatter shield is detected (block 806), or if the X-ray tube voltage is less than the threshold (block 805), at block 810 the X-ray tube 218 generates and outputs X-ray radiation. At block 812, the X-ray detector 106 (e.g., via the scintillation screen 228, the reflector 230, and the digital imaging sensor 232, and/or via a solid state panel coupled to a scintillator) captures digital image(s) (e.g., digital still images and/or digital video). The X-ray detector 106 provides the captured digital image(s) to the computing device 208.

At block 814, the computing device 208 adds the auxiliary data to the digital image(s). Example auxiliary data includes a timestamp, a date stamp, geographic data, and/or an inclination of the frame 202, the X-ray detector 206, the X-ray tube 218, and/or any other component of the digital X-ray imaging system 200. At block 816, the computing device 208 outputs the digital image(s) to the display device(s) 218 (e.g., via a wired and/or wireless connection). In some examples, the computing device 208 outputs the digital image(s) to an external computing device such as a laptop, a smartphone, a server, a tablet computer, a personal computer, and/or any other type of external computing device.

At block 818, the computing device 208 determines whether the digital image(s) are to be stored (e.g., in a storage device). If the digital image(s) are to be stored (block 818), at block 820 the example computing device 208 stores the image(s). The example computing device 208 may be configured to store the digital image(s) in one or more available storage devices, such as a removable storage device.

After storing the image(s) (block 820), or if the digital image(s) are not to be stored (block 818), control returns to block 804. In some examples, blocks 810-820 may be iterated substantially continuously until the trigger is deactivated.

Figure 9:
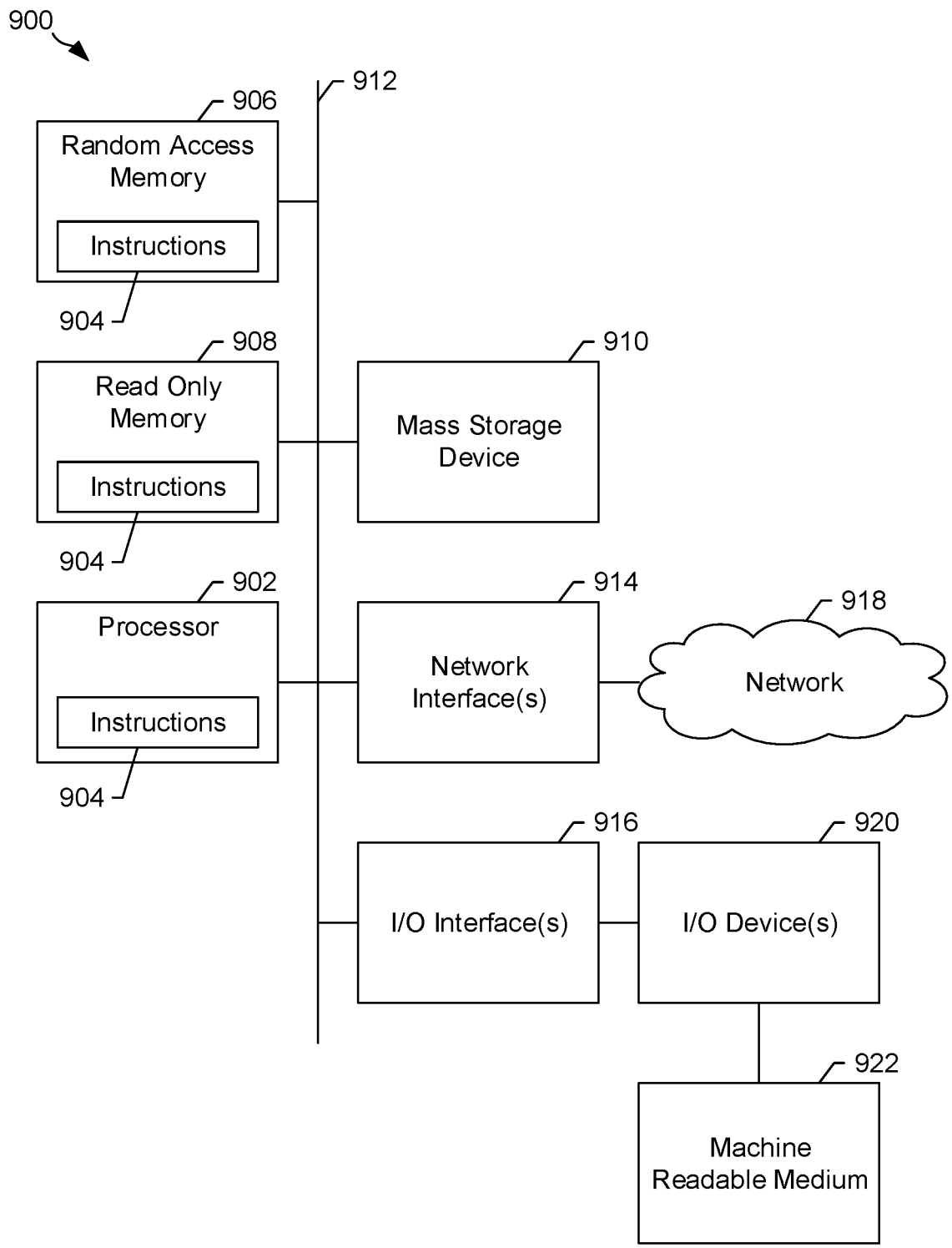
FIG. 9 is a block diagram of an example computing system that may be used to implement the computing device of FIG. 2.

FIG. 9 is a block diagram of an example computing system 900 that may be used to implement the computing device 208 of FIG. 2. The example computing system 900 may be implemented using a personal computer, a server, a smartphone, a laptop computer, a workstation, a tablet computer, and/or any other type of computing device.

The example computing system 900 of FIG. 9 includes a processor 902. The example processor 902 may be any general purpose central processing unit (CPU) from any manufacturer. In some other examples, the processor 902 may include one or more specialized processing units, such as RISC processors with an ARM core, graphic processing units, digital signal processors, and/or system-on-chips (SoC). The processor 902 executes machine readable instructions 904 that may be stored locally at the processor (e.g., in an included cache or SoC), in a random access memory 906 (or other volatile memory), in a read only memory 908 (or other non-volatile memory such as FLASH memory), and/or in a mass storage device 910. The example mass storage device 910 may be a hard drive, a solid state storage drive, a hybrid drive, a RAID array, and/or any other mass data storage device.

A bus 912 enables communications between the processor 902, the RAM 906, the ROM 908, the mass storage device 910, a network interface 914, and/or an input/output interface 916.

The example network interface 914 includes hardware, firmware, and/or software to connect the computing system 900 to a communications network 918 such as the Internet. For example, the network interface 914 may include IEEE 902.X-compliant wireless and/or wired communications hardware for transmitting and/or receiving communications.

The example I/O interface 916 of FIG. 9 includes hardware, firmware, and/or software to connect one or more input/output devices 920 to the processor 902 for providing input to the processor 902 and/or providing output from the processor 902. For example, the I/O interface 916 may include a graphics processing unit for interfacing with a display device, a universal serial bus port for interfacing with one or more USB-compliant devices, a FireWire, a field bus, and/or any other type of interface. Example I/O device(s) 920 may include a keyboard, a keypad, a mouse, a trackball, a pointing device, a microphone, an audio speaker, an optical media drive, a multi-touch touch screen, a gesture recognition interface, a display device (e.g., the display device(s) 118, 212) a magnetic media drive, and/or any other type of input and/or output device.

The example computing system 900 may access a non-transitory machine readable medium 922 via the I/O interface 916 and/or the I/O device(s) 920. Examples of the machine readable medium 922 of FIG. 9 include optical discs (e.g., compact discs (CDs), digital versatile/video discs (DVDs), Blu-ray discs, etc.), magnetic media (e.g., floppy disks), portable storage media (e.g., portable flash drives, secure digital (SD) cards, etc.), and/or any other type of removable and/or installed machine readable media.

Example wireless interfaces, protocols, and/or standards that may be supported and/or used by the network interface(s) 914 and/or the I/O interface(s) 916, such as to communicate with the display device(s) 212, include wireless personal area network (WPAN) protocols, such as Bluetooth (IEEE 802.15); near field communication (NFC) standards; wireless local area network (WLAN) protocols, such as WiFi (IEEE 802.11); cellular standards, such as 2 G/2 G+ (e.g., GSM/GPRS/EDGE, and IS-95 or cdmaOne) and/or 2 G/2 G+ (e.g., CDMA2000, UMTS, and HSPA); 4 G standards, such as WiMAX (IEEE 802.16) and LTE; Ultra-Wideband (UWB); etc. Example wired interfaces, protocols, and/or standards that may be supported and/or used by the network interface(s) 914 and/or the I/O interface(s) 916, such as to communicate with the display device(s) 212, include comprise Ethernet (IEEE 802.3), Fiber Distributed Data Interface (FDDI), Integrated Services Digital Network (ISDN), cable television and/or internet (ATSC, DVB-C, DOCSIS), Universal Serial Bus (USB) based interfaces, etc.

The processor 202, the network interface(s) 914, and/or the I/O interface(s) 916, and/or the display device 212, may perform signal processing operations such as, for example, filtering, amplification, analog-to-digital conversion and/or digital-to-analog conversion, up-conversion/down-conversion of baseband signals, encoding/decoding, encryption/decryption, modulation/demodulation, and/or any other appropriate signal processing.

The computing device 208 and/or the display device 212 may use one or more antennas for wireless communications and/or one or more wired port(s) for wired communications. The antenna(s) may be any type of antenna (e.g., directional antennas, omnidirectional antennas, multi-input multi-output (MIMO) antennas, etc.) suited for the frequencies, power levels, diversity, and/or other parameters required for the wireless interfaces and/or protocols used to communicate. The port(s) may include any type of connectors suited for the communications over wired interfaces/protocols supported by the computing device 208 and/or the display device 212. For example, the port(s) may include an Ethernet over twisted pair port, a USB port, an HDMI port, a passive optical network (PON) port, and/or any other suitable port for interfacing with a wired or optical cable.

The present methods and systems may be realized in hardware, software, and/or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. For example, block and/or components of disclosed examples may be combined, divided, re-arranged, and/or otherwise modified. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed is:

1. A portable X-ray scanner, comprising:
   an X-ray detector configured to generate images based on incident X-ray radiation;
   an X-ray tube configured to output X-ray radiation directed toward the X-ray detector; and
   a frame configured to:
      hold the X-ray detector;
      hold the X-ray tube such that the X-ray tube directs the X-ray radiation to the X-ray detector;
      enable a single user to position the X-ray detector and the X-ray tube while carrying the frame during output of the X-ray radiation; and
      enable attachment of a Compton scatter shielding device to the frame; and
   a switch configured to detect attachment of the shielding device to the frame and enable activation of the X-ray tube in response to detecting the attachment of the shielding device.

2. The portable X-ray scanner as defined in claim 1, further comprising a collimator configured to filter the output of the X-ray radiation, the switch configured to detect attachment of the shielding device adjacent the collimator.

3. The portable X-ray scanner as defined in claim 1, wherein the switch comprises a sensor configured to detect the presence of the shielding device.

4. The portable X-ray scanner as defined in claim 3, wherein the sensor comprises at least one of a mechanical switch, a capacitive sensor, an inductive sensor, a magnetic sensor, or an optical sensor.

5. The portable X-ray scanner as defined in claim 1, wherein the switch is configured to enable activation of the X-ray tube based on whether the X-ray tube is configured to use a tube voltage that satisfies a threshold tube voltage.

6. The portable X-ray scanner as defined in claim 5, wherein the threshold tube voltage is 70 kV, and the switch is configured to disable the X-ray tube when the X-ray tube is configured to use at least the threshold tube voltage and attachment of the shielding device to the frame is not detected.

7. The portable X-ray scanner as defined in claim 1, wherein the frame comprises an attachment rail configured to hold the shielding device.

8. A portable X-ray scanner, comprising:
   an X-ray detector configured to generate images based on incident X-ray radiation;
   an X-ray tube configured to output X-ray radiation; and
   a frame configured to:
      hold the X-ray detector;
      hold the X-ray tube such that the X-ray tube directs the X-ray radiation to the X-ray detector; and
      enable a single user to position the X-ray detector and the X-ray tube while carrying the frame during output of the X-ray radiation;
   a backscatter shield configured to provide shielding from Compton scatter radiation when placed in contact with an object to be scanned; and
   a switch configured to detect attachment of the backscatter shield to the frame and enable activation of the X-ray tube in response to detecting the attachment of the backscatter shield.

9. The portable X-ray scanner as defined in claim 8, wherein the switch is configured to enable activation of the X-ray tube based on whether the X-ray tube is configured to use a tube voltage that satisfies a threshold tube voltage.

10. The portable X-ray scanner as defined in claim 9, wherein the threshold tube voltage is 70 kV, and the switch is configured to disable the X-ray tube when the X-ray tube is configured to use at least the threshold tube voltage and attachment of the shielding device to the frame is not detected.

* * * * *